United States Patent [19]

Lovegrove

[11] Patent Number: 4,617,103
[45] Date of Patent: Oct. 14, 1986

[54] ELECTROPHORETIC SEPARATOR

[75] Inventor: Peter C. Lovegrove, Didcot, England

[73] Assignee: United Kingdom Atomic Energy Authority, London, England

[21] Appl. No.: 703,475

[22] Filed: Feb. 20, 1985

[30] Foreign Application Priority Data

Mar. 2, 1984 [GB] United Kingdom ................. 8405601

[51] Int. Cl.[4] ........................................... G01N 27/28
[52] U.S. Cl. ........................... 204/300 R; 204/299 R; 204/282; 204/283; 204/182.4; 204/272
[58] Field of Search ............... 204/300 R, 299 R, 282, 204/283, 182.4, 272

[56] References Cited

U.S. PATENT DOCUMENTS

| 3,616,453 | 10/1971 | Philpot | 204/300 R X |
| 3,844,926 | 10/1974 | Smyth et al. | 204/300 R X |
| 3,984,303 | 10/1976 | Peters et al. | 204/272 X |
| 4,097,357 | 6/1978 | Jacquelin | 204/272 X |
| 4,149,957 | 4/1979 | Gibson et al. | 204/299 R X |
| 4,465,583 | 8/1984 | Lovegrove | 204/299 R |

Primary Examiner—John F. Niebling
Assistant Examiner—B. J. Boggs, Jr.
Attorney, Agent, or Firm—William R. Hinds

[57] ABSTRACT

A continuous flow electrophoretic separator (10) is provided, comprising a cylindrical stator (12) and a concentric tubular rotor (14), and electrode systems (24, 26) incorporated into the stator and the rotor defining between them an annular separation chamber (28). One or both electrode systems include a tubular semi-permeable membrane (56) supported by a support tube (58) of a rigid plastics material and grooved on its inner and outer surfaces. The grooves (64, 62) are deep enough to provide fluid communication between the two surfaces of the support tube, and those grooves (64) adjacent to the separation chamber are preferably less than 3 mm wide. If the membrane (56) is between the support tube (58) and the separation chamber (28), then the support tube (58) may have both longitudinal (60) and circumferential grooves (64) adjacent the membrane, and longitudinal grooves (62) on its other surface.

11 Claims, 5 Drawing Figures

ELECTROPHORETIC SEPARATOR

This invention relates to a continuous flow electrophoretic separator.

A continuous flow electrophoretic separator comprises a cylindrical stator, a concentric tubular rotor defining an annular chamber between the stator and the rotor, an electrode system incorporated in the stator, an electrode system incorporated into the rotor, means for causing a carrier liquid to flow through the chamber, and an inlet means in the stator for injecting a migrant material into the carrier liquid. In operation, an electric field is applied radially across the annular chamber between the electrode systems, carrier liquid is caused to flow through the annular chamber, and the rotor is rotated about the stator so as to stabilise laminar flow in the chamber. Migrant material injected into the carrier liquid is thus subjected to electrophoretic separation.

An example of a continuous flow electrophoretic separator is described in UK patent specification No. 1,186,184 (U.S. Pat. No. 3,616,453), and modifications to that example are described in UK patent specification No. 1,578,809 (U.S. Pat. No. 4,149,957). Such separators may be used to fractionate an inlet stream into a plurality of outlet streams.

UK Pat. No. 1,578,809 describes a continuous flow electrophoretic separator in which each electrode system includes a semi-permeable membrane, which defines in part the annular chamber, and which is supported by a water-permeable resin-bonded cellulose fibre hollow cylinder. The water-permeable resin-bonded cellulose fibre material has adequate strength when immersed in an electrolyte to maintain dimensional stability; it can be accurately machined to small tolerances; it is not bio-degradable, and is resistant to chemical attack over a wide range of pH; and since it has a high void fraction it has a low electrical resistance when immersed in electrolyte. The advantage of the low electrical resistance is that the heat generated at the boundaries of the annular chamber is thereby reduced, such heat having a detrimental effect in causing convective mixing. The void fraction of such a resin-bonded cellulose-fibre material may be as much as 85%, so that any gas bubbles generated within the material can readily escape, rising through the pores of the material to the top of the electrode system. The pore size is typically 5 microns, so that the machined cylindrical surfaces that are adjacent to the annular chamber (one of which is covered by a semi-permeable membrane) present smooth surfaces to the carrier liquid flowing in the annular chamber and so do not cause turbulent mixing. Consequently it has been believed that the material used to support the semi-permeable membrane must have a small pore size and a high void fraction. However resin-bonded cellulose fibre material is fragile and hence easily broken when a separator is being assembled or disassembled, and cannot readily be sterilized by boiling.

According to the present invention there is provided a continuous flow electrophoretic separator as hereinbefore described, including an electrode system comprising a tubular semi-permeable membrane supported by a cylindrical support tube of a rigid plastics material, the inner and outer curved surfaces of the support tube being grooved, and the grooves being of sufficient depth to provide fluid communication between the inner surface and the outer surface of the support tube.

The support tube is considerably more robust than the known hollow cylinder of resin-bonded cellulose fibre material, and may be made of a material such as Delrin 510 AF acetal which can be sterilized in boiling water. Desirably the grooves in one surface and the grooves in the other surface have orientations crossing approximately at right angles. The grooves in one surface may be circumferential, and the grooves in the other surface longitudinal. Alternatively the grooves in one surface may be helical, and the grooves in the other surface helical with the opposite hand.

Preferably the grooves defined in the surface adjacent to the annular chamber are narrow, desirably less than about 3 mm wide.

The semi-permeable membrane may be at the surface of the support tube remote from the annular chamber, in which case the grooves on the surface adjacent the annular chamber are preferably of width about 0.5 mm and spacing about 0.5 mm. In this case, if these grooves are oriented circumferentially, desirably they slope upwardly towards the annular chamber.

Alternatively the semi-permeable membrane may be at the surface of the support tube adjacent to the annular chamber, in which case the surface of the support tube adjacent the membrane preferably defines both circumferential grooves and additional longitudinal grooves, while the other surface defines longitudinal grooves, the longitudinal grooves and the additional longitudinal grooves being defined alternately around the support tube. Desirably the bases of the additional longitudinal grooves are at a smaller radius than the bases of the longitudinal grooves, and the additional longitudinal grooves have substantially the same depth as the circumferential grooves.

An electrophoretic separator including such a support tube, with the semi-permeable membrane at the surface adjacent to the annular chamber, can operate with a lower driving voltage between the two electrode systems than can the previously known separator, and consequently with less power dissipation within the carrier liquid.

The invention will now be further described by way of example only and with reference to the accompanying drawings, in which.

Figure 1:
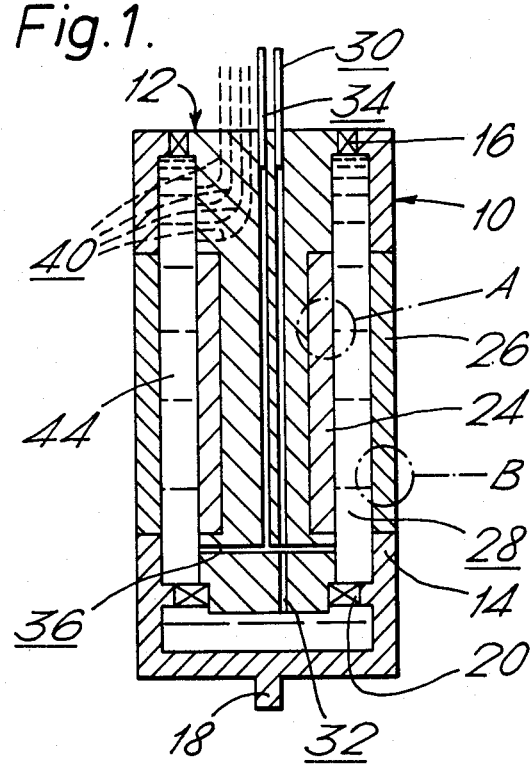
FIG. 1 is a diagrammatic medial sectional representation of an electrophoretic separator.

Referring to FIG. 1, an electrophoretic separator 10 is shown similar in principle to those described in the aforementioned patent specifications. The separator 10 comprises a rigidly mounted cylindrical stator 12, and a concentric tubular rotor 14 rotatably connected to the stator 12 by a bearing 16 at its upper end and drivable by means of a stub shaft 18 attached to the lower end of the rotor 14. The lower end of the stator 12 is spaced apart from the rotor 14 by a bearing 20 through which liquid is free to flow. The stator 12 incorporates a cylindrical electrode system 24 along a portion of its length, and the rotor 14 incorporates a tubular electrode system 26 in opposed relationship to the electrode system 24 so as to define an annular chamber 28 between the two electrode systems 24 and 26 in which, in operation of the separator 10, electrophoresis takes place. A duct 30 extends through the stator 12 to a port 32 at the lower end of the stator 12, and a duct 34 extends through the stator 12 to communicate with a slot 36 around the perimeter of the stator 12 below the lower end of the electrode system 24. Thirty discharge ducts 40 (only four of which are indicated by broken lines) extend through the stator 12 from thirty axially displaced positions on the surface of the stator 12 above the upper end of the electrode system 24. For further details with respect to the construction of the electrophoretic separator 10 reference is directed to the aforementioned specifications.

In operation of the separator 10, a potential difference is applied between the two electrode systems 24 and 26 so as to set up a radial electric field across the annular chamber 28, and the rotor 14 is rotated about the stator 12. A carrier liquid 44 is supplied down the duct 30 to the port 32, flowing through the bearing 20 and upwards between the stator 12 and rotor 14 to emerge through the discharge ducts 40. A migrant material is caused to flow down the duct 34 to emerge from the slot 36 into the carrier liquid 44, and is carried upwards through the annular chamber 28. As a result of its passage through the electric field, the migrant is electrophoretically separated into its components, which follow radially separate paths through the chamber 28, and hence emerge through different discharge ducts 40. The flow of carrier liquid 44 and migrant material through the separator 10 is thus fractionated into thirty outlet streams emerging from the thirty ducts 40.

Figure 2:
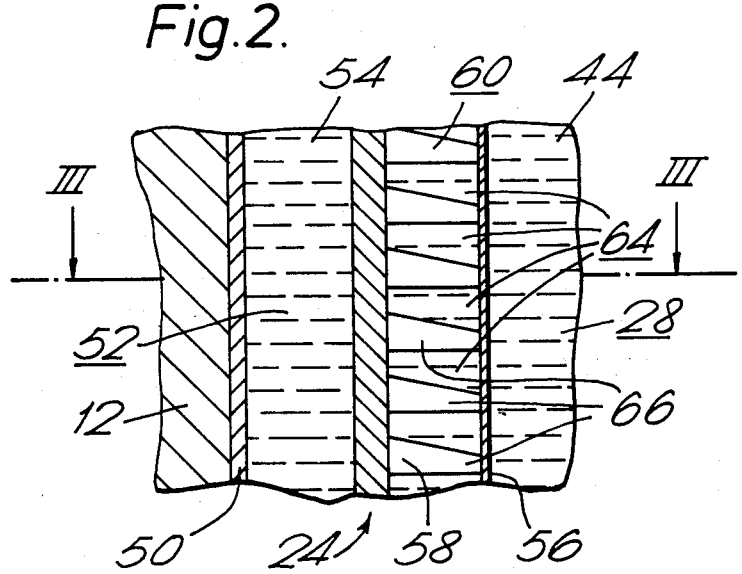
FIG. 2 is a view to an enlarged scale of the region marked A in FIG. 1.
Figure 3:
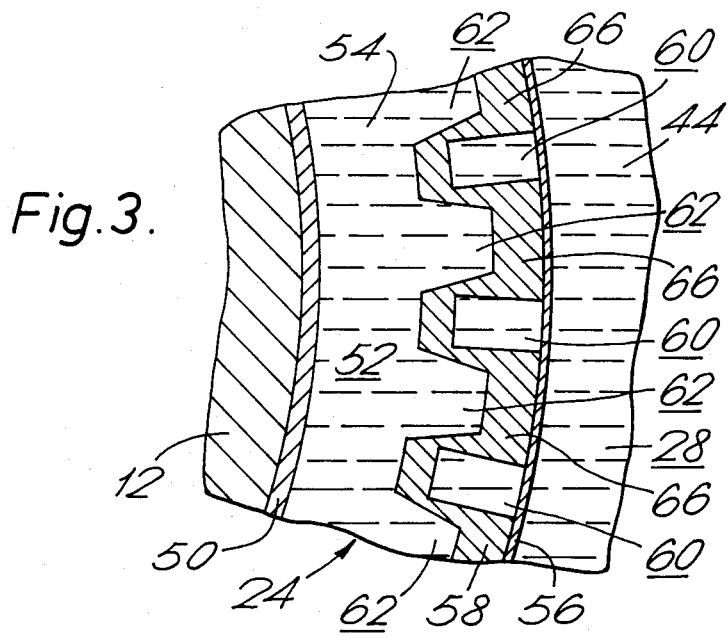
FIG. 3 is a sectional view on the line III - III of FIG. 2.

Referring now to FIGS. 2 and 3 which show an axial, and a cross-sectional view, respectively, of a part of the electrode system 24 incorporated into the stator 12, the electrode system 24 comprises a stainless steel electrode 50 at the inside wall of an annular electrode chamber 52 through which an electrolyte 54 is passed. The electrolyte 54 is separated from the carrier liquid 44 in the annular chamber 28 by a tubular semi-permeable cellulose membrane 56 supported by the outer surface of a cylindrical support tube 58 of Delrin 510AF acetal plastics material. Grooves 60 are defined along the outer surface of the support tube 58 parallel to the axis, and grooves 62 (see FIG. 3) are defined along the inner surface of the support tube 58 between adjacent grooves 60. The depths of the grooves 60 and 62 are both greater than half the thickness of the support tube 58 so that the bases of the grooves 60 are at a smaller radius from the axis than the bases of the grooves 62. Circumferential grooves 64 (see FIG. 2) of the same depth as the grooves 60 are defined around the outside surface of the support tube 58, at an axial spacing of 2 mm, each groove 64 being of mean width 2 mm and tapering towards its base. Ribs 66 are thus defined between adjacent circumferential grooves 64, the lower surface of each rib 66 being horizontal and the upper surface sloping upwardly towards the base of the adjacent groove 64.

During operation of the electrophoretic separator 10 gas bubbles are generated by electrolysis in the electrolyte 54, but any bubbles in the vicinity of the support tube 58 can readily escape by rising up the grooves 60 or 62 and so do not accumulate. Gas bubbles within the grooves 64 tend to flow into the neighbouring grooves 60 or 62, this flow being encouraged by the upward slope of the upper surface of the ribs 66. It will be appreciated that any accumulation of gas pockets within the support tube 58 would lead to a higher electrical resistance and so would be detrimental to operation of the separator 10. The carrier liquid 44 immediately adjacent to the membrane 56 is flowing approximately parallel to the axis but the grooves 64 are sufficiently narrow (and are covered by the membrane 56) that no turbulent mixing is caused.

Figure 4:
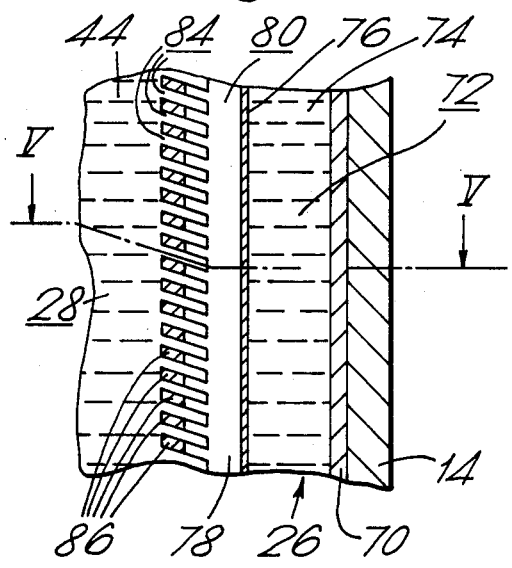
FIG. 4 is a view to an enlarged scale of the region marked B in FIG. 1.
Figure 5:
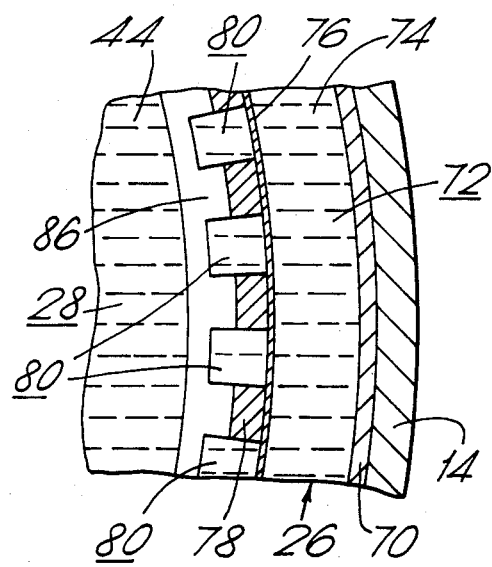
FIG. 5 is a sectional view on the line V - V of FIG. 4.

Referring now to FIGS. 4 and 5, which show an axial, and a cross-sectional view, respectively, of a part of the electrode system 26 incorporated into the rotor 14, the electrode system 26 comprises a stainless steel electrode 70 at the outside wall of an annular electrode chamber 72 through which an electrolyte 74 is passed. The electrolyte 74 is separated from the carrier liquid 44 in the annular chamber 28 by a tubular semi-permeable cellulose membrane 76 supported by the outer surface of a cylindrical support tube 78 of Delrin 510AF acetal. Grooves 80 are defined along the outer surface of the support tube 78 parallel to the axis, and narrow circumferential grooves 84 (see FIG. 4) are defined around the inner surface, each groove 84 being 0.5 mm wide, and adjacent grooves 84 defining between them circumferential ribs 86 each of axial width 0.5 mm. Both the grooves 80 and the grooves 84 are of depth greater than half the thickness of the support tube 78 so they communicate with each other. Each rib 86 and groove 84 slopes upwardly towards the inner surface of the support tube 78.

During operation of the electrophoretic separator 10 the grooves 80 and 84 are entirely filled with the carrier liquid 44. The grooves 84 are sufficiently narrow not to cause turbulent mixing of the carrier liquid 44 flowing up the annular chamber 28, and yet provide an adequately low electrical resistance path between the annular chamber 28 and the semi-permeable membrane 76. It will be appreciated that since the membrane 76 is on the outer surface of the support tube 78, it separates the support tube 78 from the electrolyte 74, and so no gas bubbles are generated within the grooves 80 and 84.

The carrier liquid 44 adjacent to the inner surface of the support tube 78 flows in a helical path up the annular chamber 28, due to the rotation of the rotor 14. To ensure turbulent mixing does not occur it may be preferable to orientate the grooves on the inner surface approximately perpendicular to the flow direction of the adjacent carrier liquid 44. In a modification (not shown) of the electrode system 26 of FIGS. 4 and 5 the inner surface of a support tube defines grooves of width 0.5 mm and spacing 0.5 mm, rectangular in cross-section, extending parallel to the axis, while the outer surface, which supports the membrane 76, defines circumferential grooves deep enough to communicate therewith.

In an alternative modification (not shown) of the electrode system 26 of FIGS. 4 and 5 the membrane 76 is held against the inner surface of a support tube (rather than the outer surface), the support tube differing from the support tube 78 only in having grooves alternately on its inner and outer surfaces extending parallel to the axis. The membrane 76 may be held in position by a small pressure difference (about 30 cm of water or less) between the carrier liquid 44 and the electrolyte 74. In this case the circumferential grooves 84 do not have to be as narrow as in the electrode system of FIGS. 4 and 5, and can extend in planes perpendicular to the longitudinal axis.

I claim:

1. A continuous flow electrophoretic separator comprising a cylindrical stator, a concentric tubular rotor defining an annular chamber between the stator and the rotor, an electrode system incorporated in the stator, an electrode system incorporated into the rotor, means for causing a carrier liquid to flow through the chamber, and an inlet means in the stator for injecting a migrant material into the carrier liquid, wherein one of the electrode systems comprises a tubular semi-permeable membrane supported by a cylindrical support tube of a rigid plastics material, the inner and outer curved surfaces of the support tube defining grooves of sufficient depth to provide fluid communication between the inner surface and the outer surface of the support tube.

2. An electrophoretic separator as claimed in claim 1 wherein the grooves defined in the surface of the support tube adjacent to the annular chamber are less than about 3 mm wide.

3. An electrophoretic separator as claimed in claim 1 wherein the grooves in one surface of the support tube and the grooves in the other surface of the support tube have orientations crossing approximately at right angles.

4. An electrophoretic separator as claimed in claim 3 wherein the grooves in one surface of the support tube are circumferential, and the grooves in the other surface of the support tube are longitudinal.

5. An electrophoretic separator as claimed in claim 1 wherein the grooves in one surface of the support tube are helical, and the grooves in the other surface of the support tube are helical with the opposite hand.

6. An electrophoretic separator as claimed in claim 1 wherein the semi-permeable membrane is at the surface of the support tube remote from the annular chamber, and the grooves on the surface adjacent the annular chamber are of width about 0.5 mm and spacing about 0.5 mm.

7. An electrophoretic separator as claimed in claim 1 wherein the semi-permeable membrane is at the surface of the support tube remote from the annular chamber, and the grooves on the surface adjacent the annular chamber are oriented circumferentially and slope in the carrier liquid flow direction towards the annular chamber.

8. An electrophoretic separator as claimed in claim 1 wherein the semi-permeable membrane is at the surface of the support tube adjacent to the annular chamber, and the surface of the support tube adjacent the membrane defines both circumferential grooves and additional longitudinal grooves, while the other surface of the support tube defines longitudinal grooves; the longitudinal grooves and the additional longitudinal grooves being defined alternately around the support tube.

9. An electrophoretic separator as claimed in claim 8 wherein the additional longitudinal grooves have substantially the same depth as the circumferential grooves, such that the sum of the depth of the longitudinal grooves and the depth of the additional longitudinal grooves exceeds the thickness of the support tube.

10. An electrophoretic separator as claimed in claim 1 wherein the other electrode system also comprises a tubular semi-permeable membrane supported by a cylindrical support tube of a rigid plastics material, the inner and the outer surfaces of the support tube being grooved, and the grooves being of sufficient depth to provide fluid communication between the inner surface and the outer surface of the support tube.

11. An electrophoretic separator as claimed in claim 10 wherein the semi-permeable membrane of each electrode system is at the surface of the respective support tube adjacent to the annular chamber.

* * * * *